(12) United States Patent
Mehl et al.

(10) Patent No.: US 11,045,238 B2
(45) Date of Patent: Jun. 29, 2021

(54) BONE SCREW IMPLANT FOR SACROILIAC JOINT FUSION

(71) Applicant: Life Spine, Inc., Huntley, IL (US)

(72) Inventors: David T. Mehl, Lake in the Hills, IL (US); Ali H. Mesiwala, Claremont, CA (US)

(73) Assignee: LIFE SPINE, INC., Huntley, IL (US)

( * ) Notice: Subject to any disclaimer, the term of this patent is extended or adjusted under 35 U.S.C. 154(b) by 197 days.

(21) Appl. No.: 16/447,945

(22) Filed: Jun. 20, 2019

(65) Prior Publication Data

US 2019/0388131 A1 Dec. 26, 2019

Related U.S. Application Data

(60) Provisional application No. 62/687,339, filed on Jun. 20, 2018.

(51) Int. Cl.
| | |
|---|---|
| *A61B 17/86* | (2006.01) |
| *A61B 17/70* | (2006.01) |
| *A61B 17/16* | (2006.01) |
| *A61F 2/28* | (2006.01) |
| *A61F 2/44* | (2006.01) |
| *A61F 2/30* | (2006.01) |

(52) U.S. Cl.
CPC .......... *A61B 17/86* (2013.01); *A61B 17/7055* (2013.01); *A61B 17/863* (2013.01); *A61B 17/1671* (2013.01); *A61B 17/7001* (2013.01); *A61F 2/28* (2013.01); *A61F 2/4455* (2013.01); *A61F 2002/30622* (2013.01); *A61F 2002/30995* (2013.01)

(58) Field of Classification Search
CPC . A61B 17/86; A61B 17/7055; A61B 17/1671; A61B 17/863
See application file for complete search history.

(56) References Cited

U.S. PATENT DOCUMENTS

| 4,940,467 | A | * | 7/1990 | Tronzo | A61B 17/8875 606/66 |
|---|---|---|---|---|---|
| 8,721,694 | B2 | * | 5/2014 | Patterson | A61B 17/863 606/300 |
| 9,358,057 | B1 | * | 6/2016 | Whipple | A61B 17/8805 |
| 2013/0018427 | A1 | * | 1/2013 | Pham | A61B 17/7055 606/301 |

(Continued)

FOREIGN PATENT DOCUMENTS

EP 3123970 A1 2/2017

*Primary Examiner* — Christian A Sevilla
(74) *Attorney, Agent, or Firm* — Foley & Lardner LLP

(57) ABSTRACT

A bone screw for sacroiliac joint fusion is characterized by a longitudinal bone screw and a cylindrical sleeve received on a proximal end of the bone screw. The sleeve has axially extending fins or flutes on its outer surface that extend generally from one end of the sleeve to the other end of the sleeve. This feature allows the sleeve to resist reverse rotation which, in turn, aids in preventing back-out of the bone screw once installed. The bone screw has a self-tapping tip that allows the bone screw to be installed without need for a pilot hole, and self-harvesting geometry that gathers and retains bone shavings in and along the bone screw that are produced by bone screw installation for use as graft for bone fusion.

15 Claims, 15 Drawing Sheets

(56) References Cited

U.S. PATENT DOCUMENTS

| | | | | |
|---|---|---|---|---|
| 2015/0012051 A1* | 1/2015 | Warren | ............. | A61B 17/8685 |
| | | | | 606/310 |
| 2016/0287301 A1 | 10/2016 | Mehl et al. | | |
| 2018/0042652 A1* | 2/2018 | Mari | .................. | A61B 17/8685 |
| 2018/0360512 A1* | 12/2018 | Mari | .................... | A61B 17/864 |
| 2019/0290341 A1* | 9/2019 | Loftus | ................ | A61B 17/8625 |
| 2020/0100823 A1* | 4/2020 | Gault | ................ | A61B 17/8635 |

\* cited by examiner

BONE SCREW IMPLANT FOR SACROILIAC JOINT FUSION

CROSS-REFERENCE TO RELATED APPLICATIONS

This U.S. non-provisional patent application claims the benefit of and/or priority under 35 U.S.C. § 119(e) to U.S. provisional patent application Ser. No. 62/687,339 filed Jun. 20, 2018 titled "Bone Screw Implant for Sacroiliac Joint Fusion" the entire contents of which is specifically incorporated herein by reference.

FIELD OF THE INVENTION

The present invention relates to bone screws for the spine and related anatomy and, more particularly, to bone screws for sacroiliac joint fusion and related anatomy.

BACKGROUND OF THE INVENTION

Bone screws are used routinely for repairing, stabilizing, fixing, fusing and other orthopedic purposes of bones of the body such as the spine and pelvis. However, no matter where bone screws are used, they face challenges of "backing out" of the anatomy in which they are installed. Bone screw malfunction such as backing out can compromise the integrity of the orthopedic purpose for which the bone screws were installed and/or pose serious risks and/or complications for the implant recipient.

In view of the above, it is therefore desirous to have a bone screw that can minimize or eliminate backing out.

SUMMARY OF THE INVENTION

A bone screw implant for sacroiliac joint fusion includes a bone screw and a self-contained rectilinear sleeve, the sleeve configured to resist reverse rotation of the bone screw once installed to help prevent screw back-out, the bone screw having self-drilling tip geometry that allows the bone screw to be installed without need for a pilot hole, and self-harvesting geometry that gathers and retains bone shavings generated by bone screw installation in the bone screw for use as graft for bone fusion.

The sleeve has non-radial (axial) geometry on its external surface that aids in resisting rotational forces exerted on the implant when fully seated into the bone (in situ). The anti-rotation geometry press fits linearly into the bony anatomy surrounding the bone screw to fix its rotational position. In one form, the anti-rotation geometry comprises tapered fins. In another form, the anti-rotational geometry comprises tapered flutes. In yet another form, the anti-rotational geometry comprises non-tapered flutes. Other geometries are contemplated.

The sleeve also has geometry that provides permanent assembly onto the bone screw and which binds/connects itself to/at a specific axial position on the bone screw to help prevent bone screw back-out. In one form, the sleeve has an inner radial groove within its inner diameter that engages a circumferential projection (e.g. ring) on the bone screw that allows the sleeve to be captured by the bone screw, while also allowing the sleeve to freely rotate with respect to the bone screw.

The freely rotating sleeve allows the sleeve to be press-fit linearly into the bone while the bone screw threads into the bone until both components are fully seated into the bone. In order for the bone screw to back out of the bone, the threads would have to rotationally loosen while also overcoming shear forces due to the presence of the press-fit condition/connection of the sleeve to the end of the bone screw.

The bone screw may include external threads on its proximal end for interfacing with a screwdriver. The proximal threads provide a secure attachment interface with the screwdriver so that the bone screw does not inadvertently disengage from the screwdriver while installing the bone screw into the bone.

The sleeve may additionally include threads on its inner surface proximate to the proximal end of the sleeve that engage the external threads on the proximal end of the bone screw. The combination of these thread forms on both components are coupled with a set screw for a secondary mechanism locking the two components together once the bone screw has been fully seated within the bone. The set screw would further prevent the bone screw from backing out and "pushing" the sleeve linearly out of the bone.

The self-drilling bone screw tip geometry is characterized by a plurality of cutting tips or blades situated about a central opening. This geometry allows the surgeon to eliminate operative steps, thus shortening surgical time.

The self-harvesting geometry is characterized by helical cutting flutes and windows situated at various intervals within the helical flute geometry that harvest bone/bone shavings (autograft) during insertion of the bone screw into the boney anatomy. Particularly, as the bone screw is rotated into the boney anatomy, the helical cutting flutes gather and deposit bone shavings into the windows. In one form, the windows comprise round and/or oval holes. In another form, the windows comprise slots. In all cases, the windows can be perpendicular with respect to the long axis of the bone screw, angular with respect to the long axis of the bone screw, formed in a helical pattern with respect to the helical trajectory of the helical cutting flutes, and/or a combination thereof. This feature solves the current challenges of pre-packing the bone screw/implant with graft biologic prior to implantation or inserting graft biologic into the bone screw/implant through an axial cannula of the bone screw after final implantation.

BRIEF DESCRIPTION OF THE DRAWING FIGURES

The features of the invention will be better understood by reference to the accompanying drawings, wherein.

DETAILED DESCRIPTION OF THE INVENTION

Figure 1:
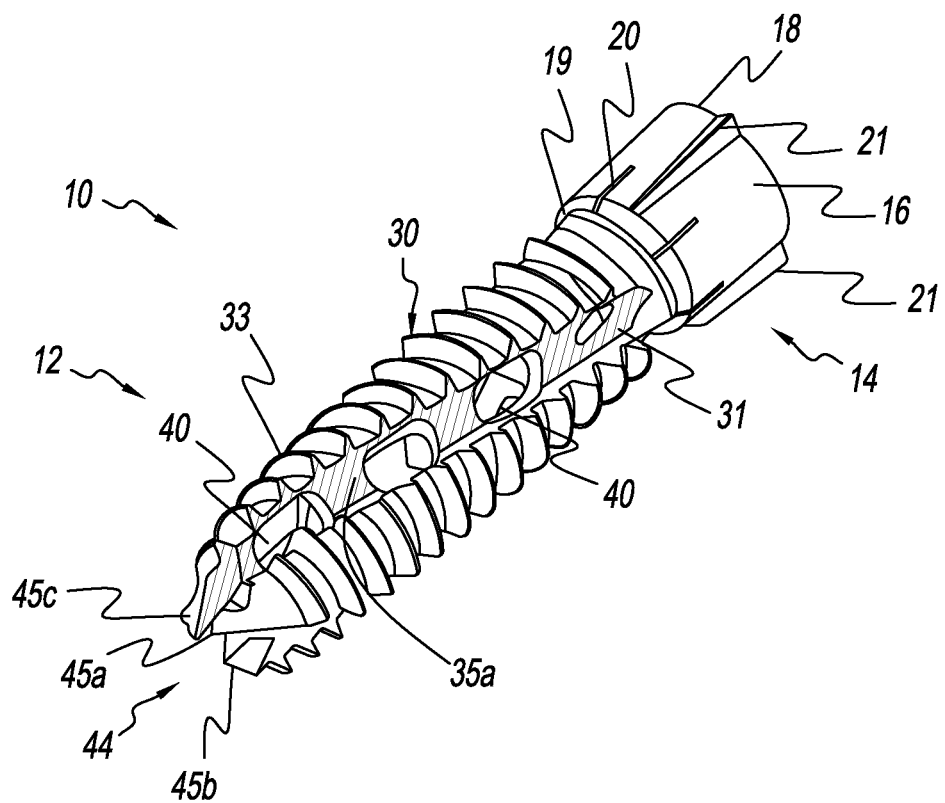
FIG. 1 is an isometric view of a bone screw implant fashioned in accordance with the principles of the present invention.
Figure 2:
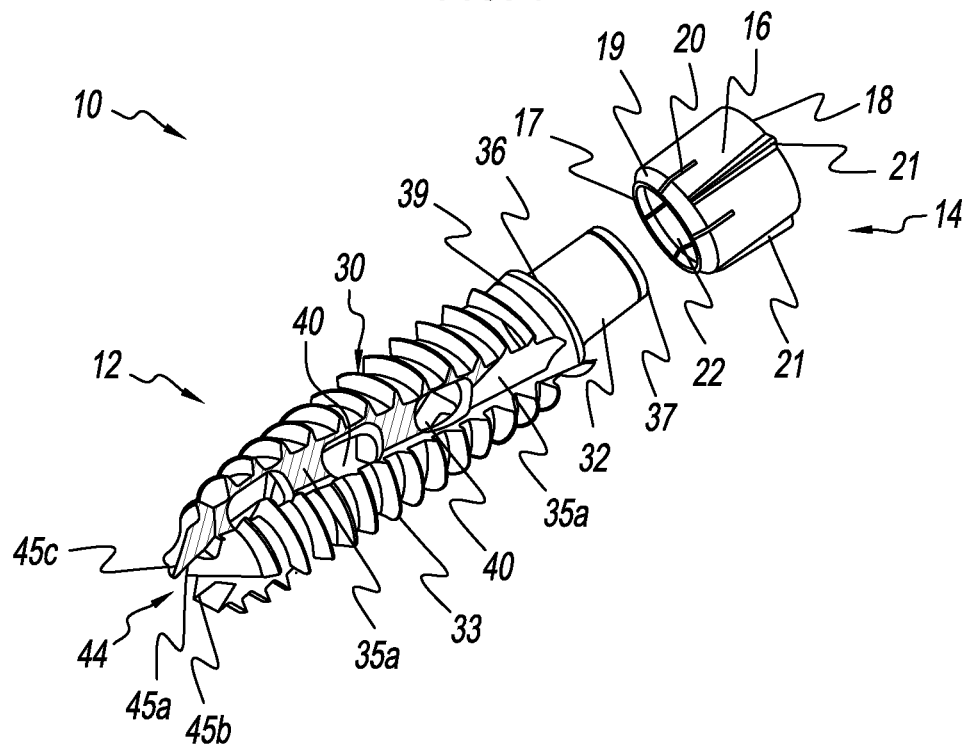
FIG. 2 is an exploded isometric view of the bone screw implant of FIG. 1.
Figure 3:
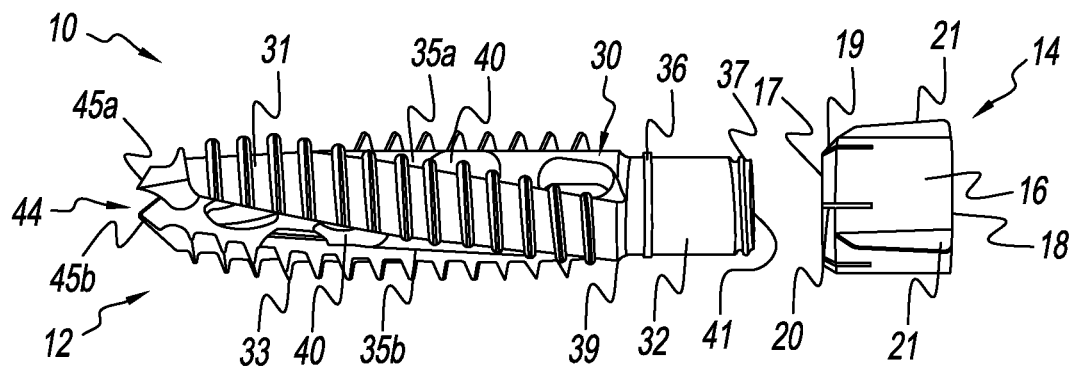
FIG. 3 is an exploded side view of the bone screw implant of FIG. 1.
Figure 4:
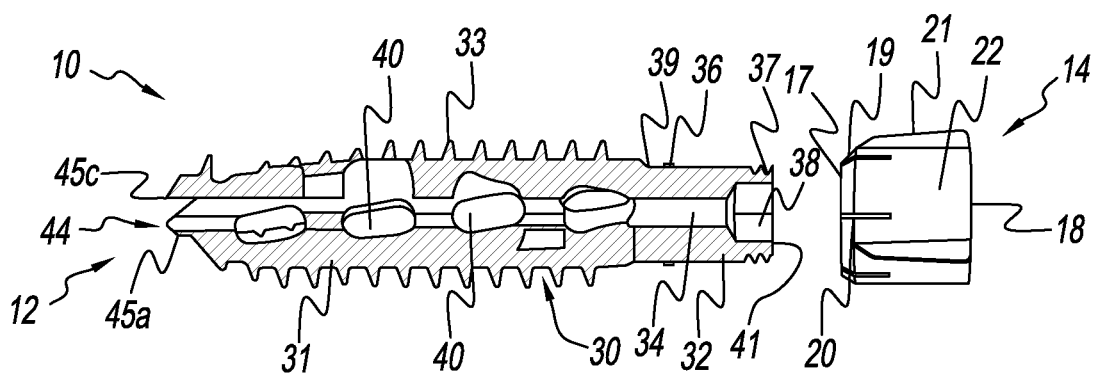
FIG. 4 is an exploded side sectional view of the bone screw implant of FIG. 1.
Figure 5:
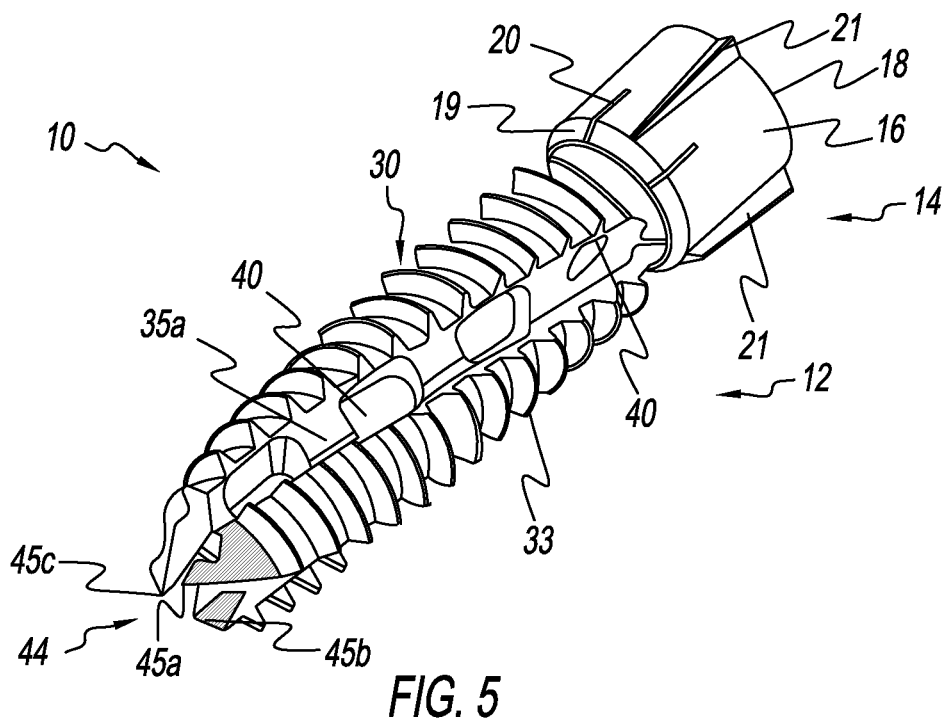
FIG. 5 is another isometric view of the bone screw implant of FIG. 1.
Figure 6:
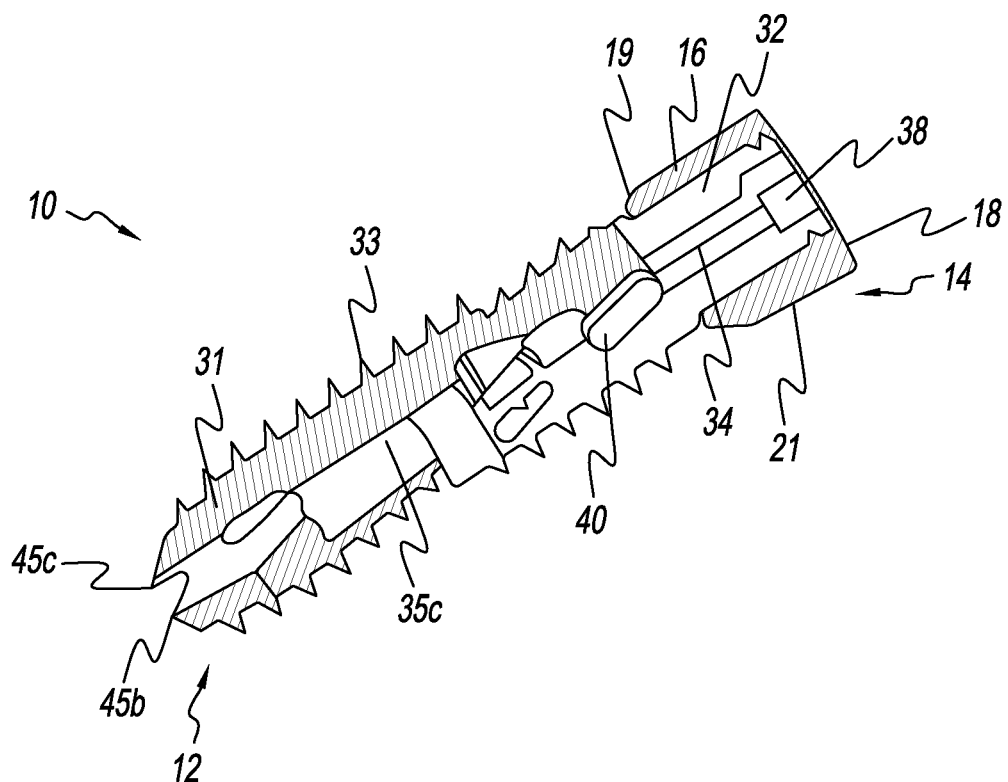
FIG. 6 is an isometric sectional view of the bone screw implant of FIG. 1.
Figure 7:
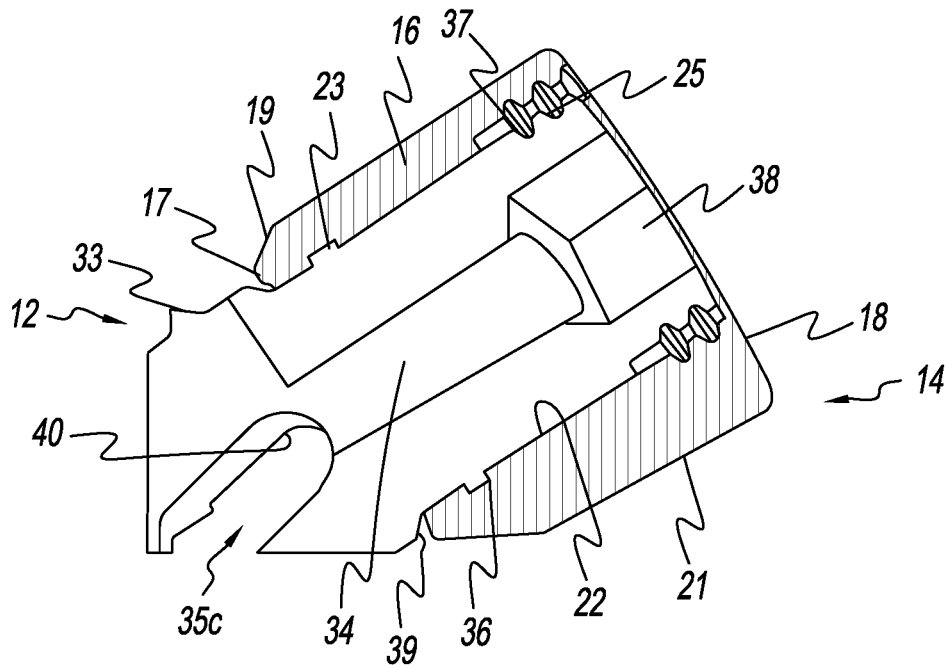
FIG. 7 is an enlarged sectional view of the proximal end of the bone screw and sleeve of the bone screw implant of FIG. 1.

For the purposes of promoting an understanding of the principles of the present disclosure, reference will now be made to the embodiments illustrated in the drawings, and specific language will be used to describe the same. It will nevertheless be understood that no limitation of the scope of this database is thereby intended.

Figure 8:
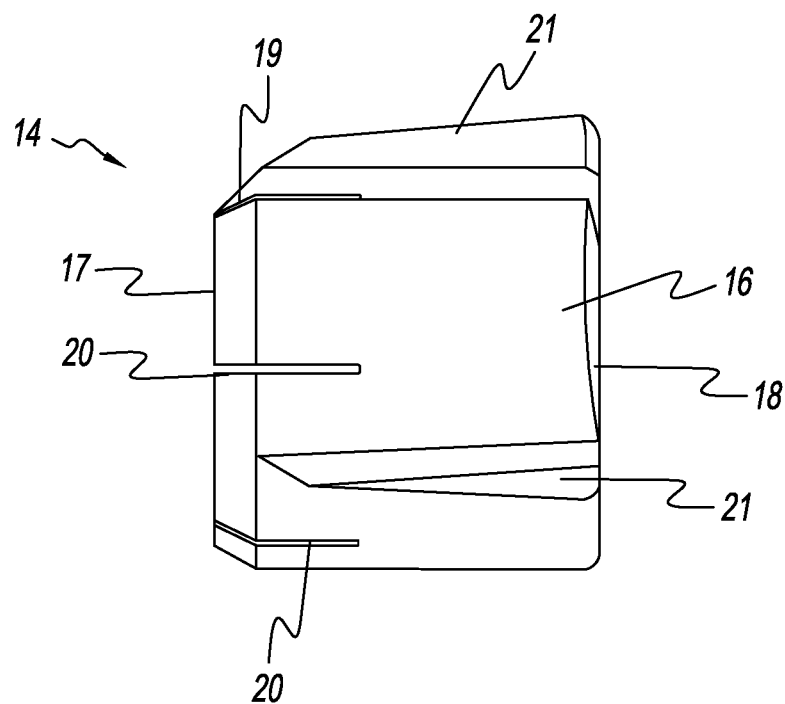
FIG. 8 is a side view of the sleeve of the bone screw implant of FIG. 1.
Figure 9:
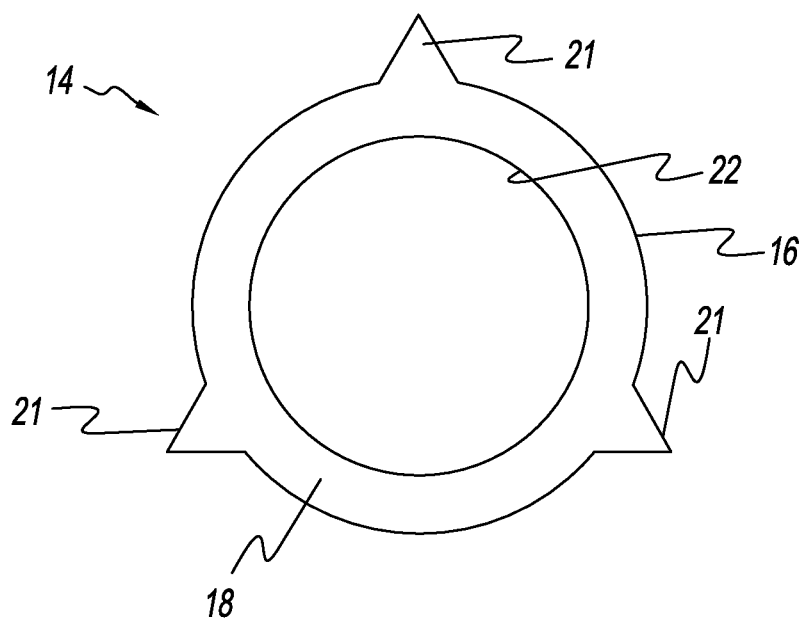
FIG. 9 is an end view of the sleeve of the bone screw implant of FIG. 1.
Figure 10:
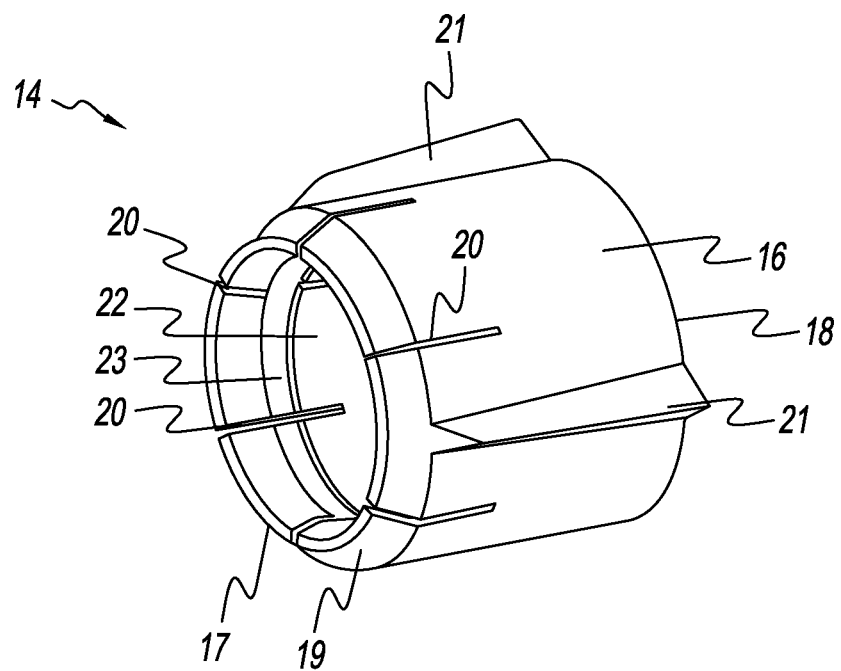
FIG. 10 is an isometric view of the sleeve of the bone screw implant of FIG. 1.
Figure 11:
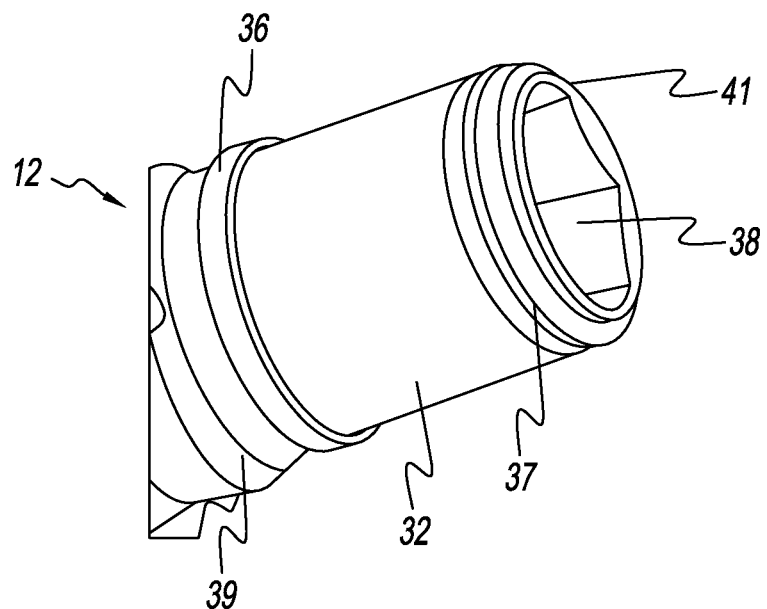
FIG. 11 is an enlarged view of the proximal end of the bone screw of the bone screw implant of FIG. 1.
Figure 12:
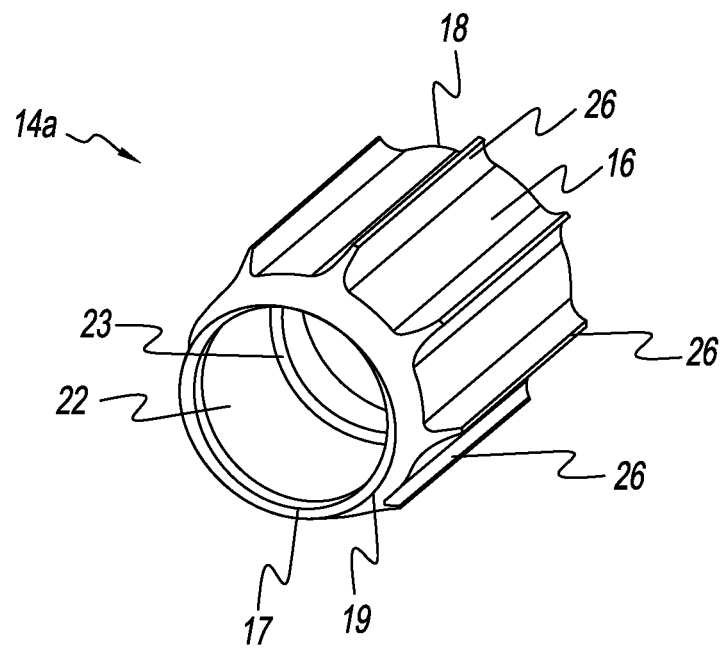
FIG. 12 is an isometric view of an alternate sleeve for the bone screw implant of FIG. 1.
Figure 13:
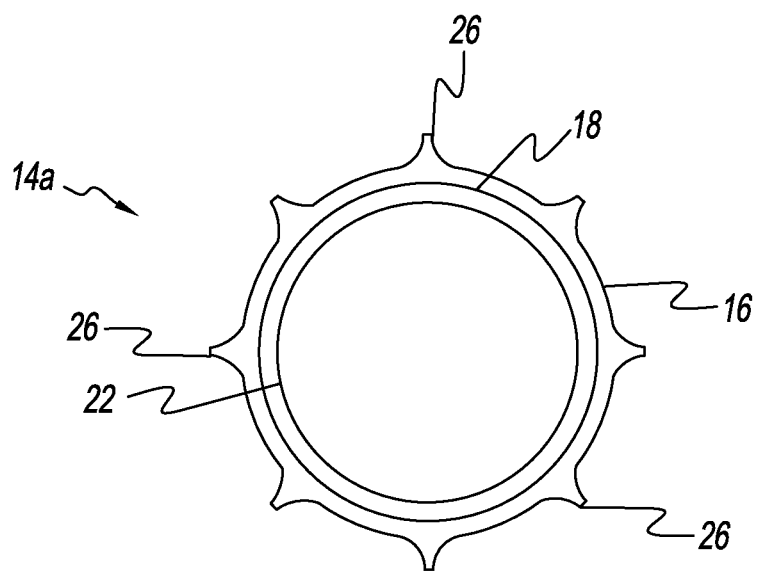
FIG. 13 is an end view of the alternate sleeve of FIG. 12.
Figure 14:
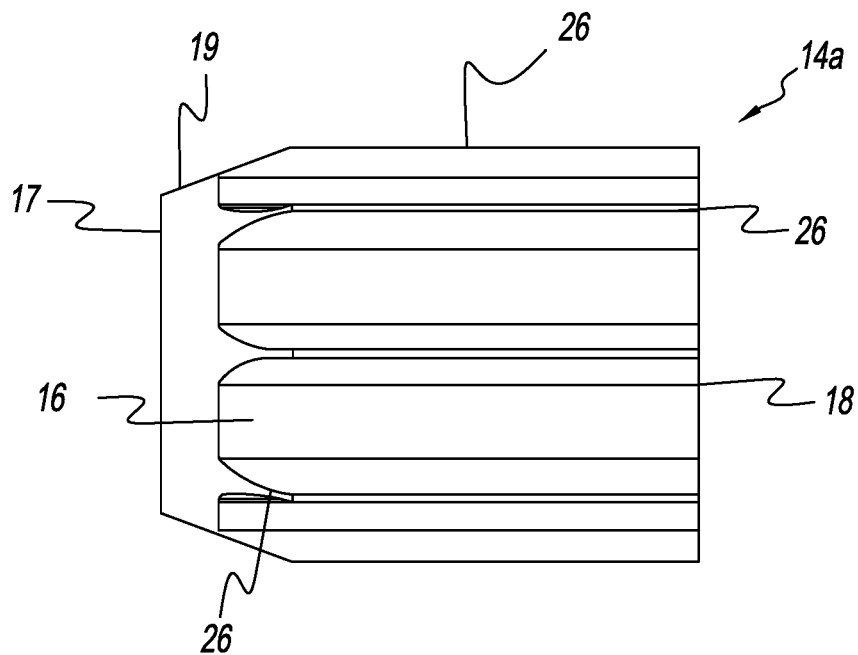
FIG. 14 is a side view of the alternate sleeve of FIG. 12.
Figure 15:
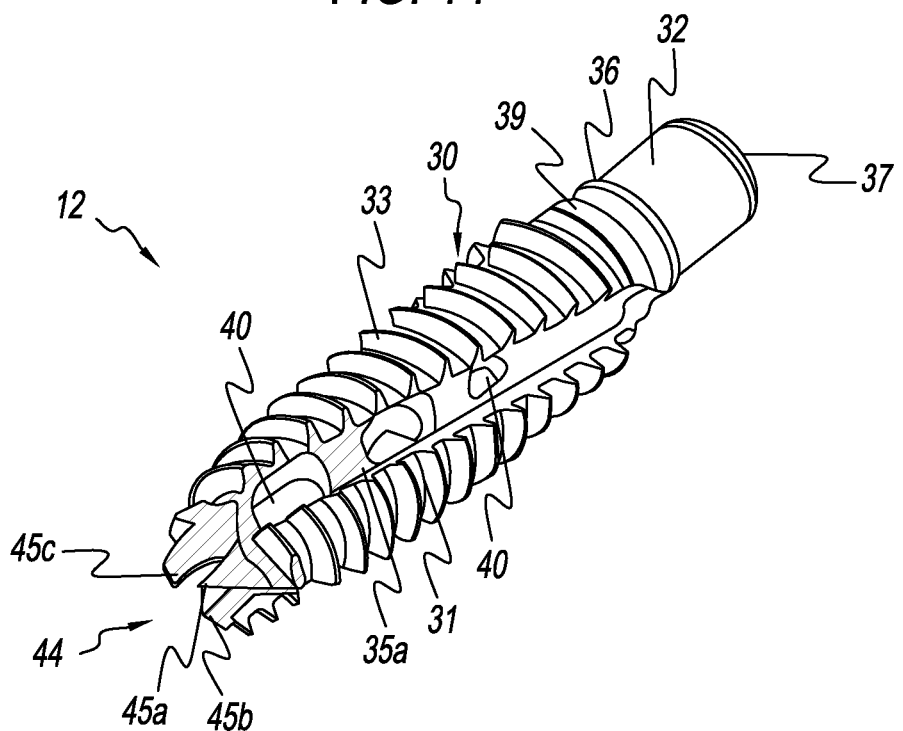
FIG. 15 is an isometric view of the bone screw of the bone screw implant of FIG. 1.
Figure 16:
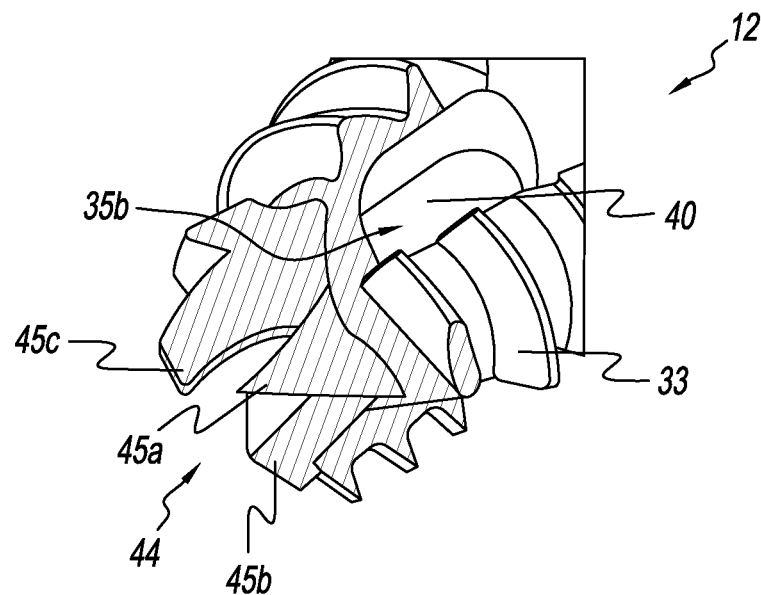
FIG. 16 is an enlarged view of the distal end (tip) of the bone screw of the bone screw implant of FIG. 1.
Figure 17:
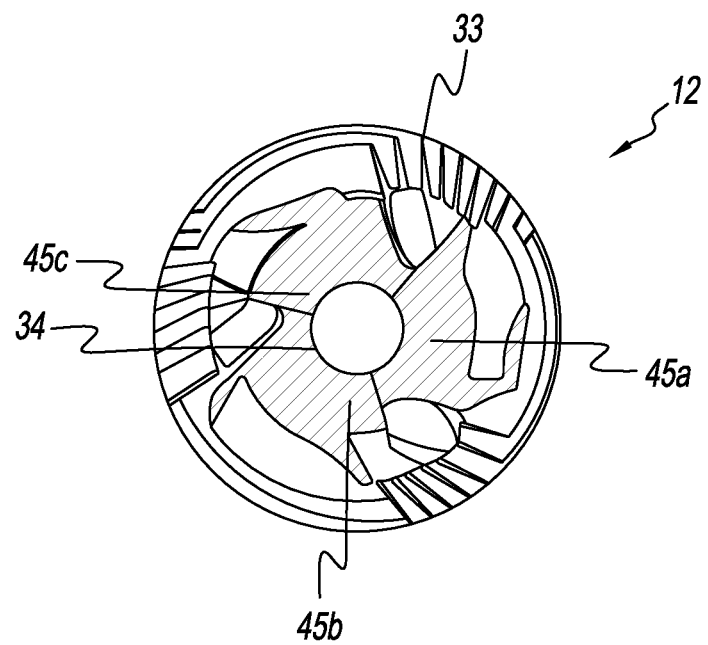
FIG. 17 is an end view of the distal end of the bone screw of the bone screw implant of FIG. 1.
Figure 18:
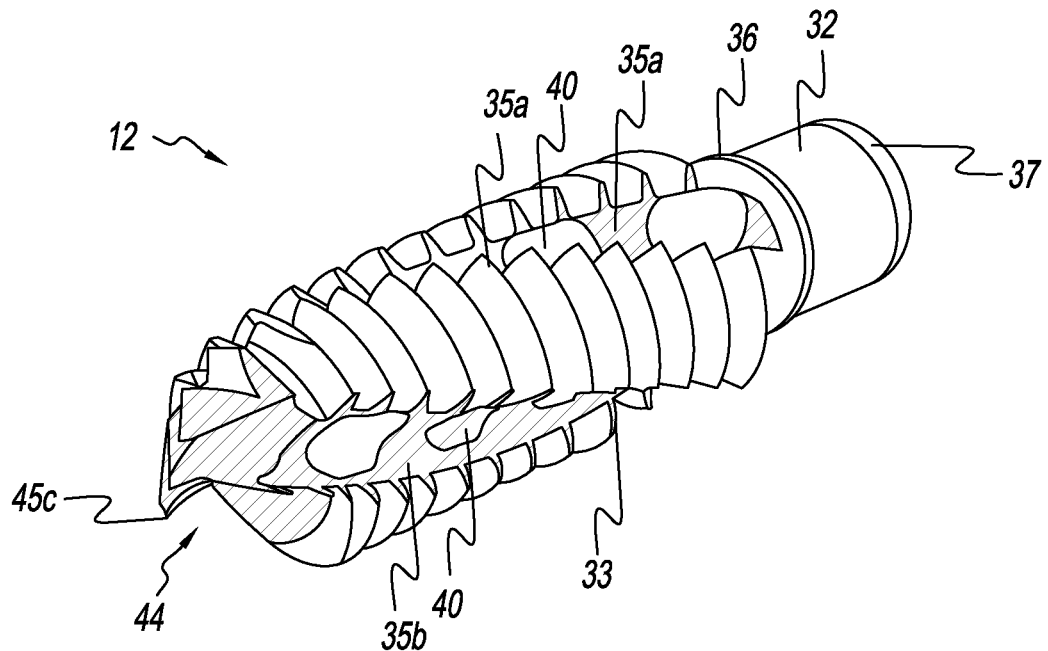
FIG. 18 is an enlarged isometric view of the bone screw of the bone screw implant of FIG. 1.
Figure 19:
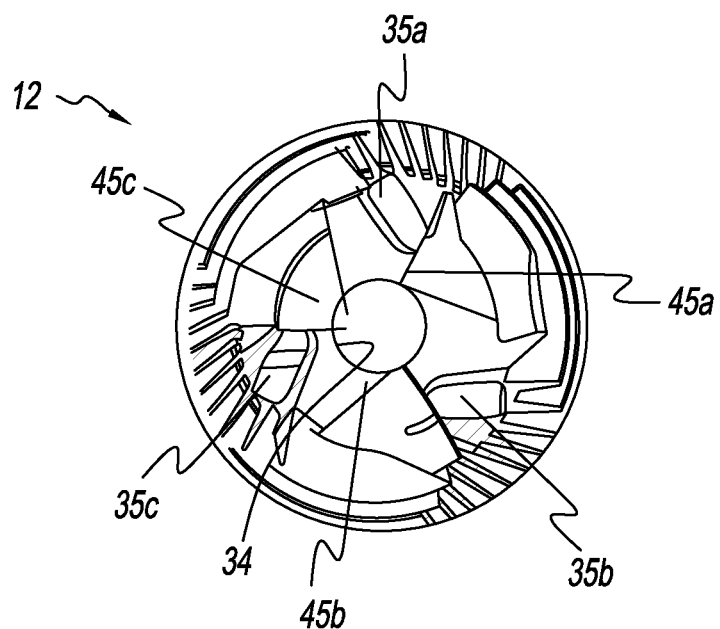
FIG. 19 is an enlarged end view of the distal end (tip) of the bone screw of the bone screw implant of FIG. 1.
Figure 20:
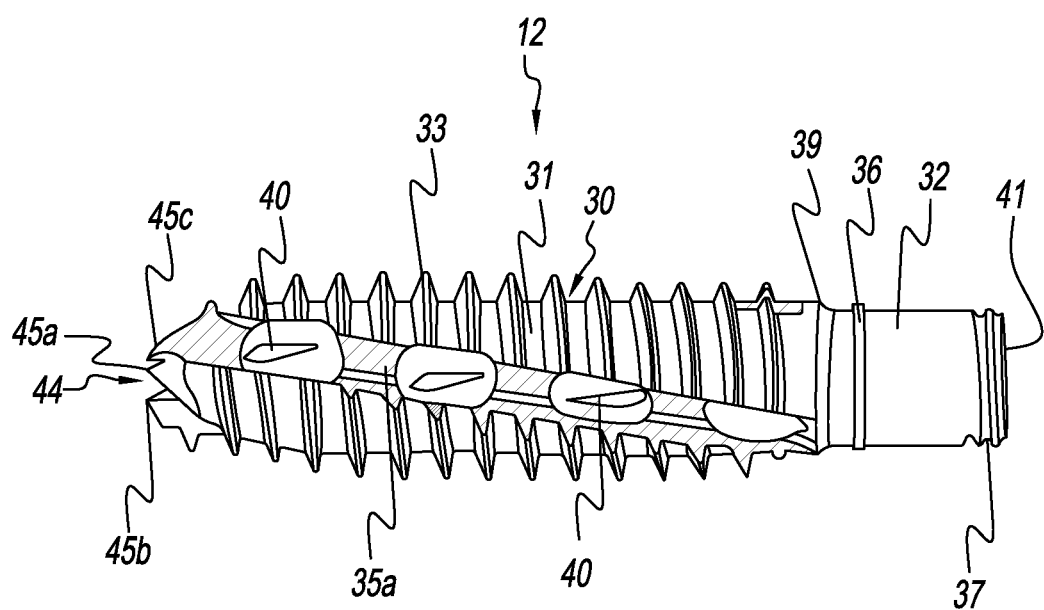
FIG. 20 is an enlarged side view of the bone screw of the bone screw implant of FIG. 1.
Figure 21:
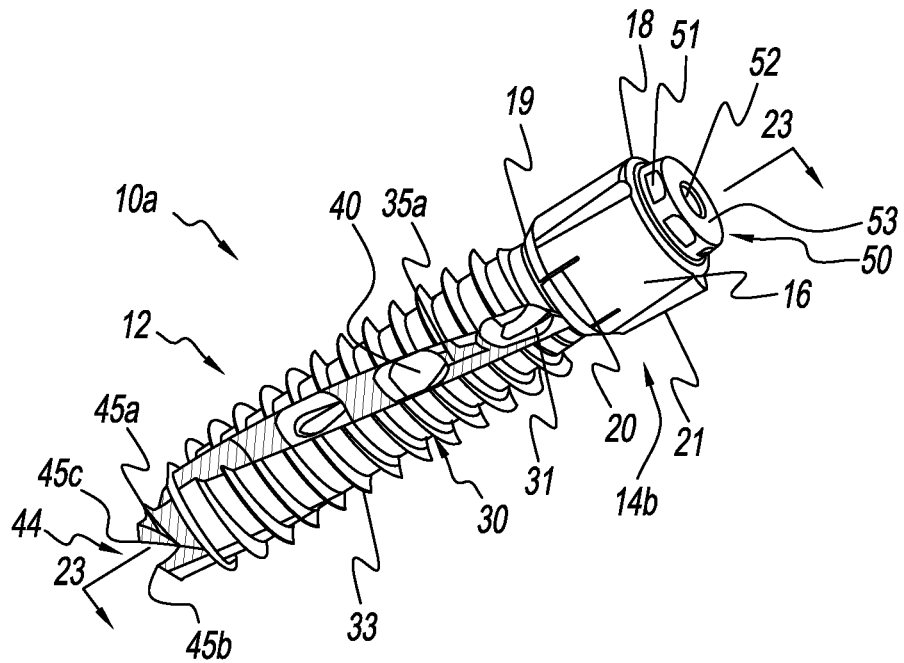
FIG. 21 is an isometric view of another bone screw implant fashioned in accordance with the present principles.
Figure 22:
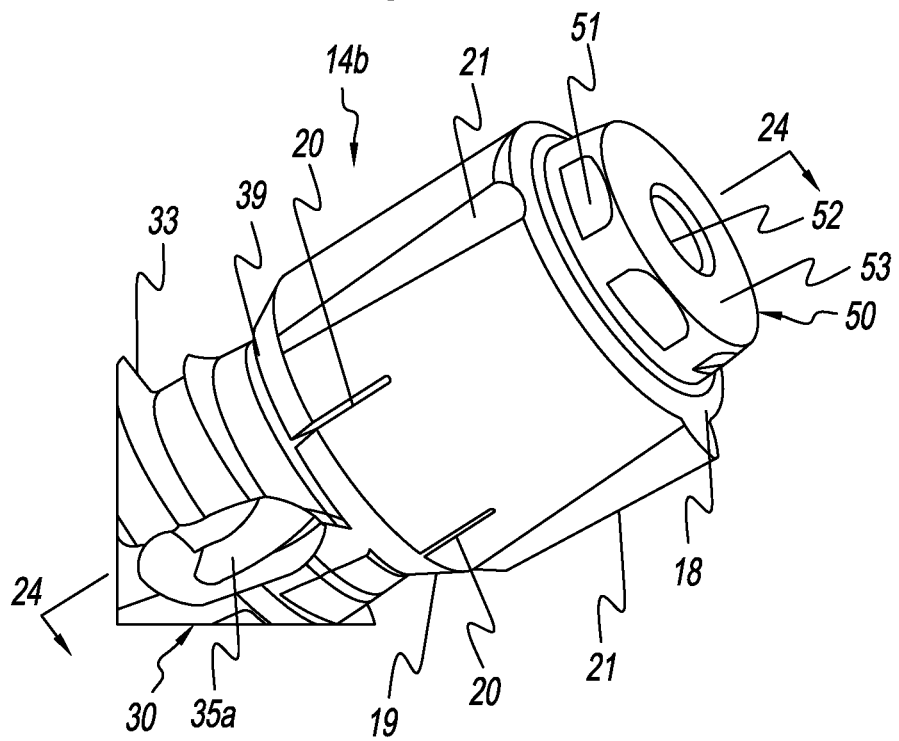
FIG. 22 is an enlarged view of the proximal end of the bone screw implant of FIG. 21.
Figure 23:
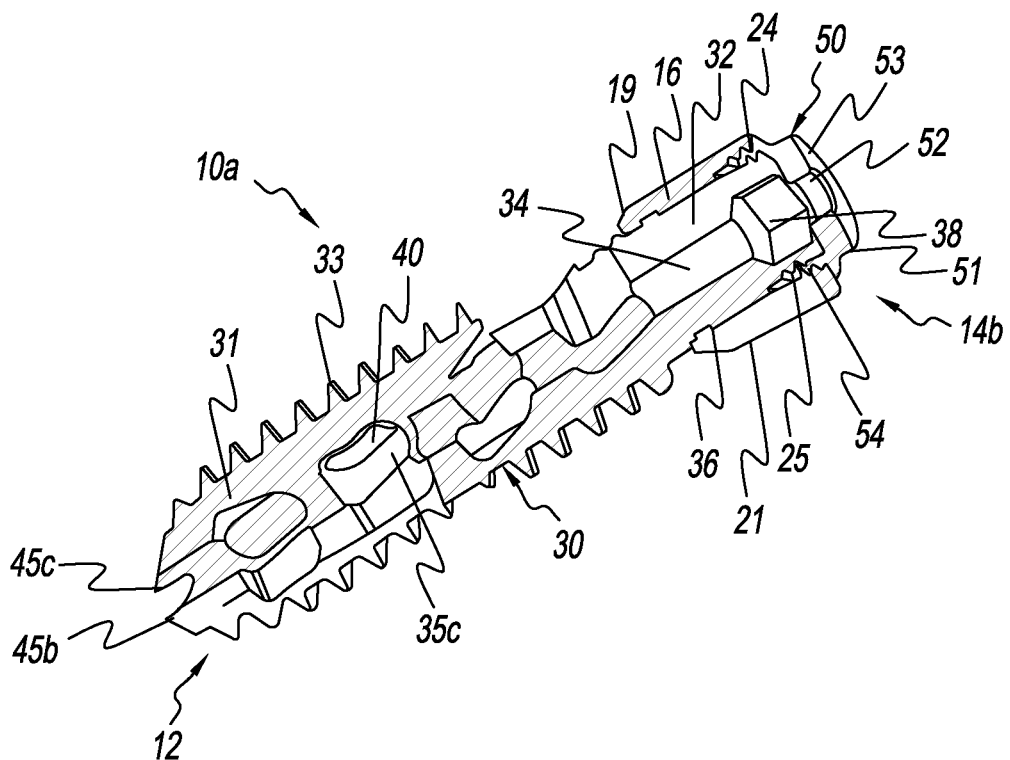
FIG. 23 is a sectional view of the bone screw implant of FIG. 21 taken along line 23-23 thereof.
Figure 24:
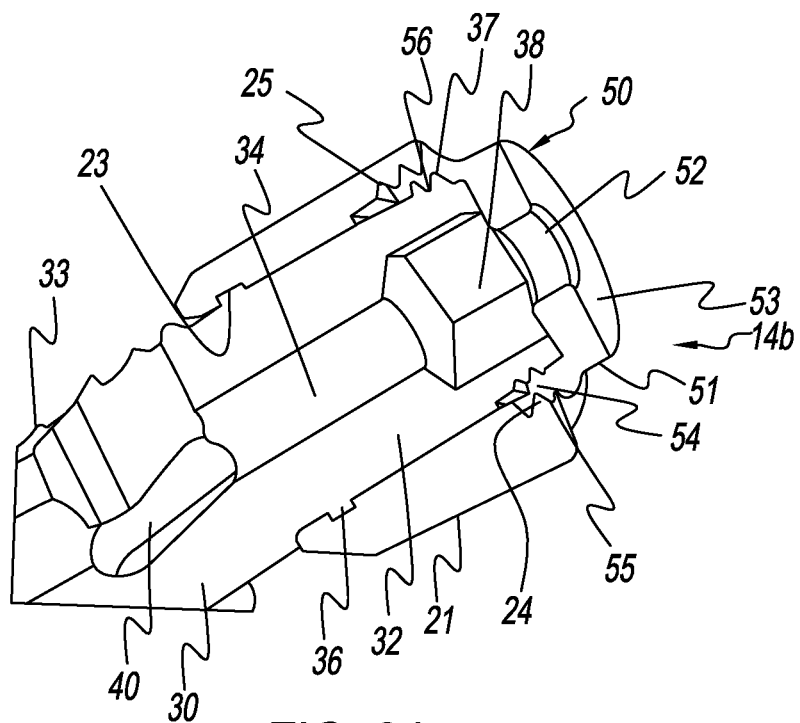
FIG. 24 is a sectional view of the proximal end of the bone screw implant of FIG. 22 taken along line 24-24 thereof.
Figure 25:
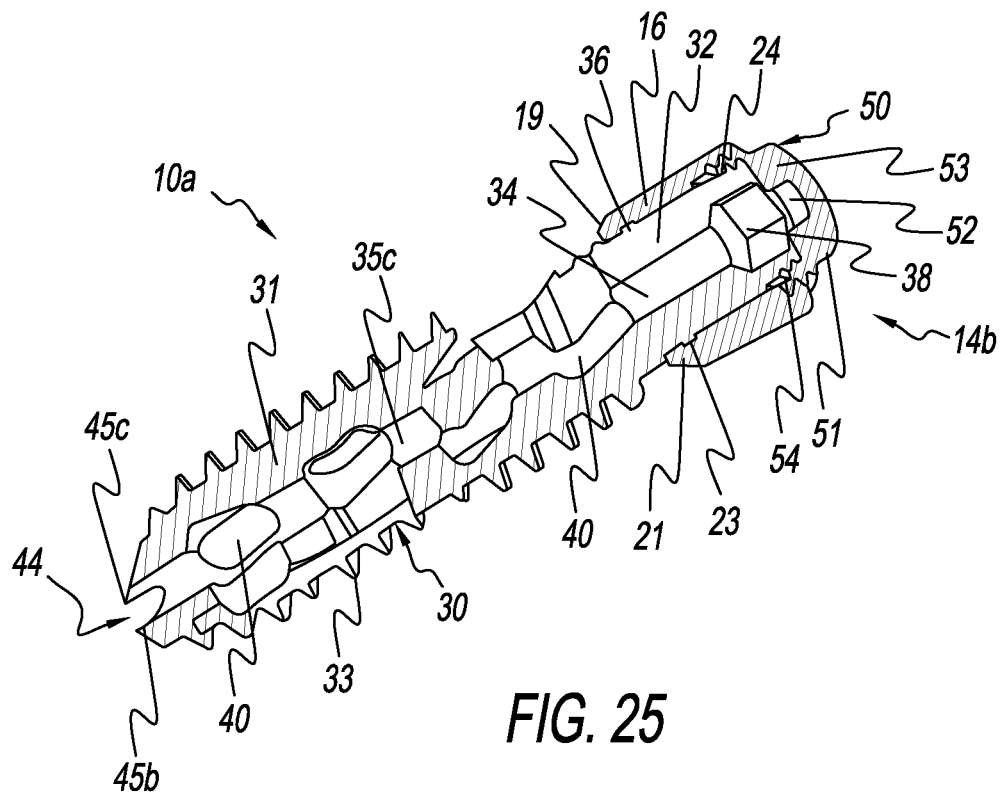
FIG. 25 is another sectional view of the bone screw implant of FIG. 21.
Figure 26:
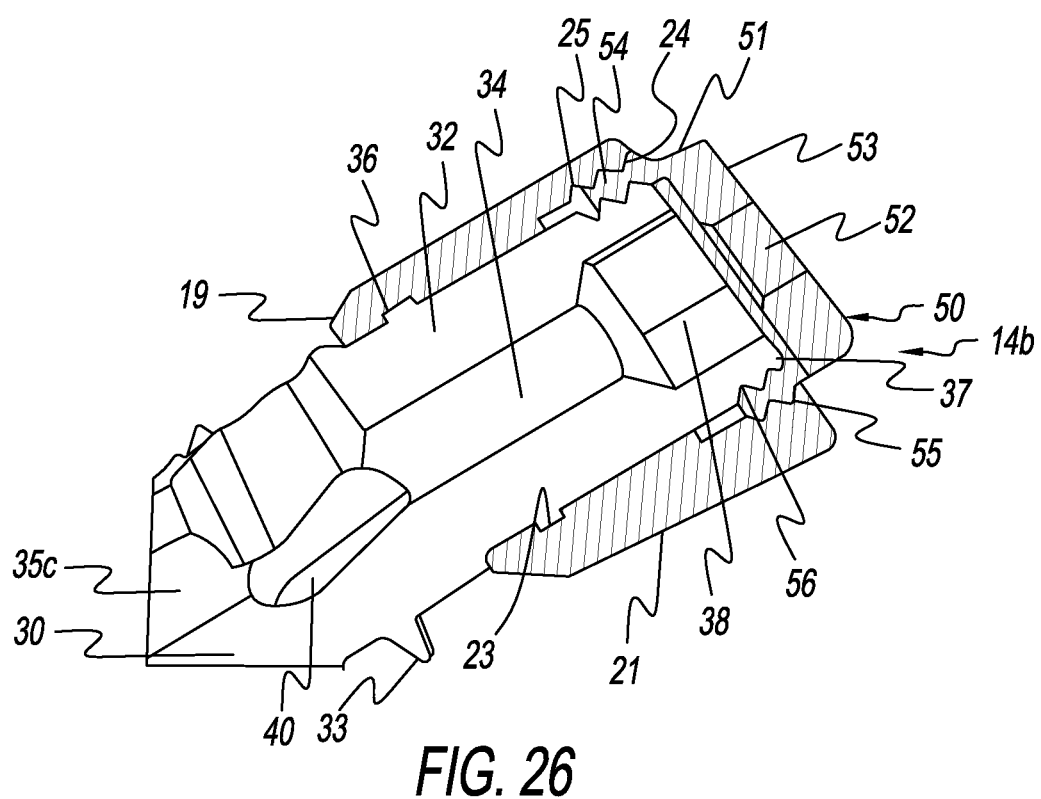
FIG. 26 is another sectional view of the proximal end of the bone screw implant of FIG. 21.
Figure 27:
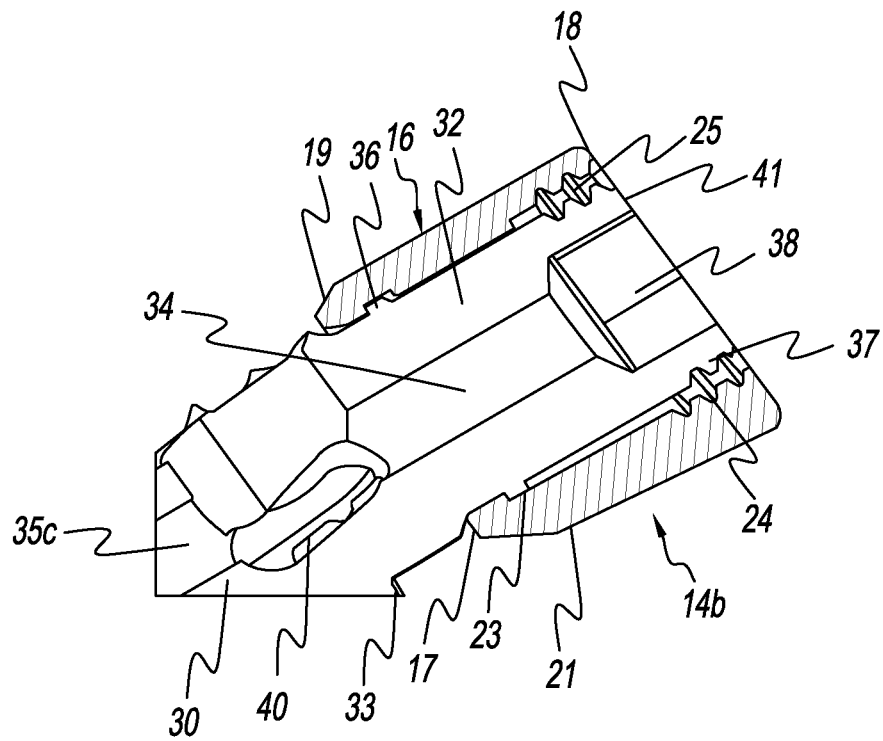
FIG. 27 is a sectional view of the proximal end of the bone screw implant of FIG. 21 without the set screw.
Figure 28:
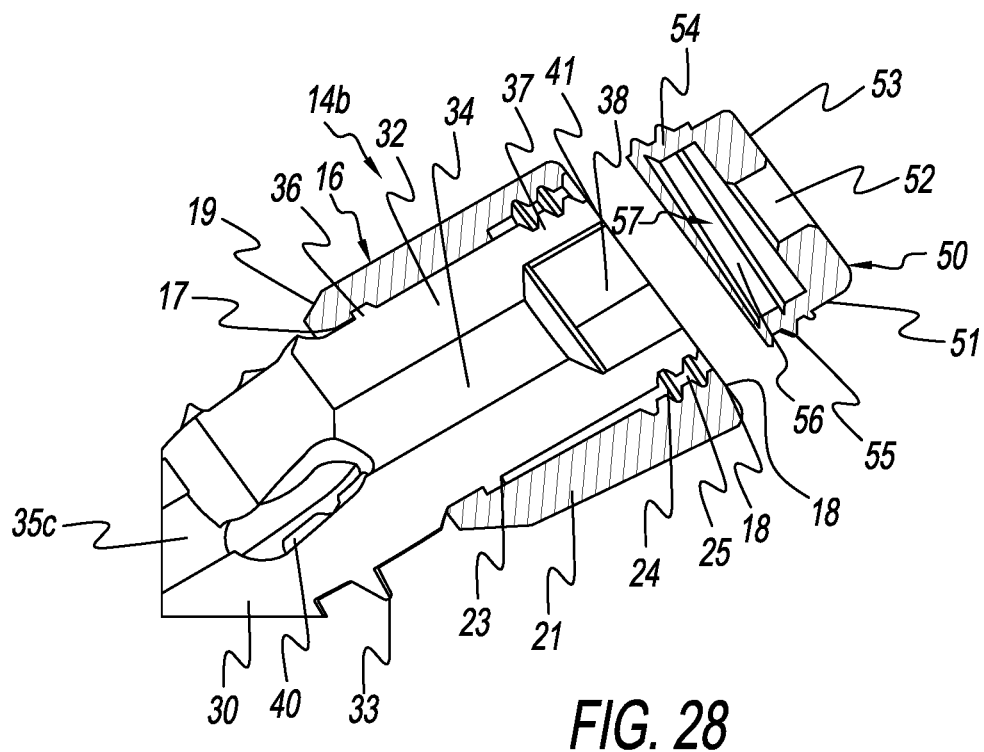
FIG. 28 is a sectional view of the proximal end of the bone screw implant of FIG. 21 with the set screw shown exploded therefrom.
Figure 29:
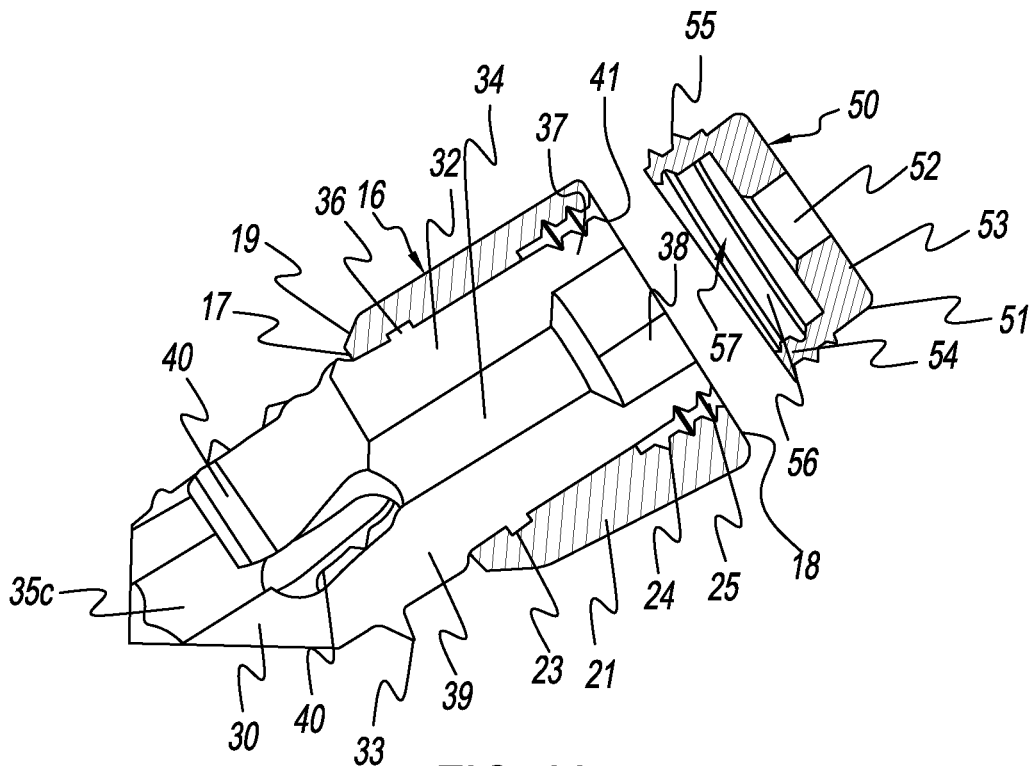
FIG. 29 is another sectional view of the proximal end of the bone screw implant of FIG. 21 with the set screw shown exploded therefrom.
Figure 30:
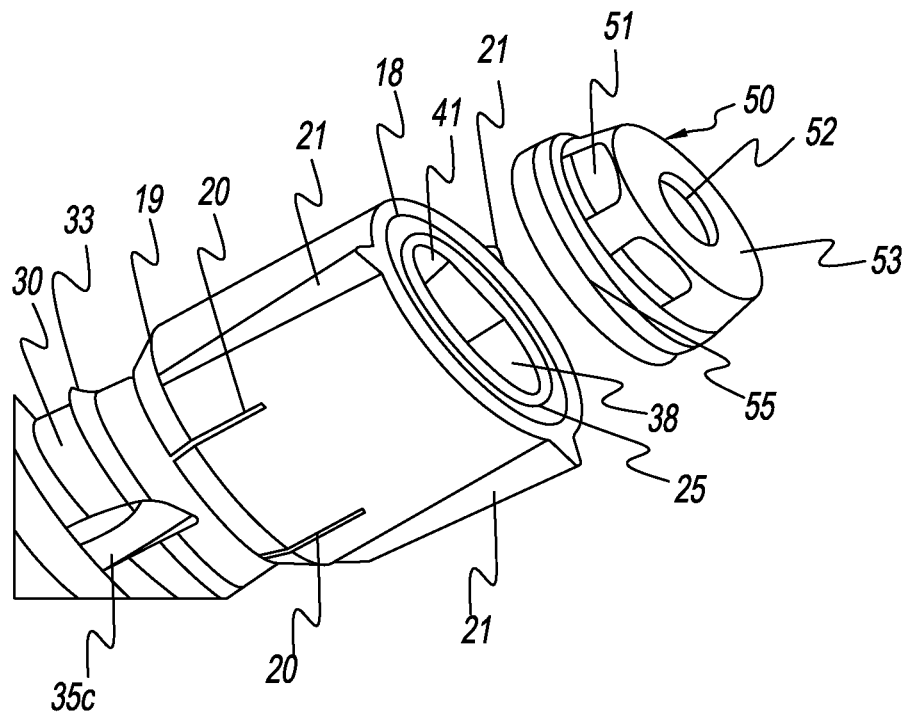
FIG. 30 is an enlarged view of the proximal end of the bone screw implant of FIG. 21 with the set screw shown exploded therefrom.

FIGS. 1-7 depict various exploded and non-exploded views of a bone screw implant 10 fashioned in accordance with the present principles, characterized by a bone screw 12 and a sleeve 14. FIGS. 11 and 15-20 depict various views of the bone screw 12. FIGS. 8-10 depict various views of the sleeve 14, while FIGS. 12-14 depict various views of an alternate sleeve 14a. The bone screw implant 10 is best used for sacroiliac fusion, but may be used for various spine applications as well as other orthopedic applications.

The bone screw 12 is characterized by a body 30 having a self-drilling or self-tapping tip 44 at its distal end and may include external threading 37 adjacent the proximal end 41 of the body 30, and particularly situated about an upper portion of the unthreaded tubular end section 32. The body 30 defines a longitudinal or long axis and length between the tip 44 and the end 41 and includes external threads/threading 33 on an outer surface thereof extending generally from the tip/distal end 44 to the end section 32. An internal cannula 34 preferably, but not necessarily, extends the entire longitudinal length of the body 30, and intersects with a socket 38 in the upper cylindrical section 32 of the body 30, providing communication between the tip 44 and the socket 38. The socket 38 is configured to receive a like-configured tool (not shown) for use in implanting the bone screw implant 10. The external surface of the upper section 32 of the body 30 has a ridge, projection, annulus, ring or the like (collectively, ring) 36 that extends about the circumference of the upper section 32 proximate a neck 39 between the upper section 32 and the external threading 33 of the body. The ring 36 may be continuous (congruent) as shown, or may be discontinuous (non-congruent) such as is formed by a plurality of ring sections (not shown). The ring 36 engages an inner radial groove 23 in an inner diameter 22 of the sleeve 14 (see, e.g. FIG. 7) the co-action allowing the sleeve 14 to be captured by the bone screw 12.

The tip 44 of the bone screw 12 (see, e.g. FIGS. 15-20) is self-drilling, and is formed of several (e.g. a plurality of) cutting blades, heads or the like 45a, 45b, 45c, it being understood that the tip 44 may comprise more or less cutting points 45. The cutting blades 45a-c are situated about an opening of the cannula 34 at the tip 44, and are preferably, but not necessarily, equally radially spaced about the cannula opening. Each blade 45a-c is configured to drill, cut or otherwise dig into bone.

The bone screw 12 has self-harvesting geometry that gathers and retains bone shavings generated by bone screw installation for use as graft for bone fusion. To this end, the bone screw 12 has several (e.g. a plurality of) preferably, but not necessarily, helical cutting channels, grooves, flutes or the like (collectively, flutes) 35a, 35b, 35c extending through the threading 33 of the bone screw body 30 from the tip 44 to the upper section 32. One helical cutting flute 35 is associated with one cutting blade 45, such that the cutting blade 45a is associated with the helical cutting flute 35a, the cutting blade 45b is associated with the helical cutting flute 35b, and the cutting blade 45c is associated with the helical cutting flute 35c. Each cutting flute 35 has a plurality of windows, openings, holes or the like (collectively, windows) 40 situated at various intervals within the helical flute geometry that together harvest bone/bone shavings (autograft) during insertion of the bone screw into the boney anatomy. Particularly, as the bone screw 12 is rotated into the boney anatomy, the helical cutting flutes 35 gather and deposit bone shavings into the windows 40. In one form, the windows 40 are round and/or oval holes. In another form, the windows 40 are slots. In all cases, the windows 40 can be perpendicular with respect to the long axis of the bone screw, angular with respect to the long axis of the bone screw, formed in a helical pattern with respect to the helical trajectory of the helical cutting flutes, and/or a combination thereof.

The sleeve 14 is characterized by a generally cylindrical body 16 defining a front 17, an end 18, and an interior, bore, or the like 22. The front 17 of the body 16 has a taper, angle, or slant (collectively, taper) 19 that circumferentially surrounds the front 17, the taper 19 providing a transition from the body 30 of the bone screw 12 to the sleeve 14 for ease in installation/implantation. The sleeve 14 has an anti-rotation feature that performs the function of resisting rotation of the implant (screw assembly) 10 when fully seated into the bone, the anti-rotation feature comprising three (3)

fins or the like 21 on the outside of the body 16, each fin 21 projecting radially outward from and extending axially along the outer surface of the body 16. Each fin 21 is preferably, but not necessarily, tapered from the front thereof (proximate the front 17 of the body 16) to the rear thereof (at or proximate the rear 18 of the body 16). The external fins 21 are also preferably, but not necessarily, equally spaced about the outer circumference of the body 16. It should be appreciated that in all instances, the number of external fins 21 may be more or less than three (3). The body 16 further has a plurality of slits, slots, channels or the like (collectively, slits) 20 that are situated about the radial circumference/diameter of the body at the front 17 thereof. Each slit 20 extends axially along the body 16 from the front 17 to a distance into the body. The slits 20 allow resilient expansion (then contraction) of the front portion of the sleeve 14 so that the ring 36 of the bone screw 12 can be received in the groove 23 of the sleeve 14 in a snap-fit fashion.

The inside of the sleeve 14 has a radial groove, slot, channel, cutout or the like (collectively, groove) 23 that preferably, but not necessarily, extends the full circumference or diameter about or around the inner surface of the bore 22 proximate the front 17. The radial groove 23 is sized to receive the ring 36 of the bone screw 12. Particularly, the radial groove 23 of the sleeve 14 receives the ring 36 of the bone screw 12 such that the bone screw 12 captures the sleeve 14 while also allowing the sleeve 14 to freely rotate with respect to the bone screw 12. The freely rotating sleeve allows the sleeve to be press-fit linearly into a receiving bone (not shown) while the bone screw threads into the receiving bone until both components are fully seated in the receiving bone.

FIGS. 12-14 depict an alternative sleeve 14a for the bone screw 12/implant 10. The sleeve 14a is a variation of the sleeve 14. Particularly, the sleeve 14a has a variation of its anti-rotation feature. However, other features, components and the like are the same as the sleeve 14 and therefore such same and/or similar features, components and the like have the same call-out number as the sleeve 14. The sleeve 14a has a plurality of flutes or the like 26 on the outside of the body 16, each flute 26 projecting radially outward from and extending axially along the outer surface of the body 16. Each flute 26 may be tapered from the front thereof (proximate the front 17 of the body 16) to the rear thereof (at or proximate the rear 18 of the body 16) or not. The external flutes 26 are also preferably, but not necessarily, equally spaced about the outer circumference of the body 16. It should be appreciated that in all instances, the number of external flutes 26 may be more or less than that shown.

FIGS. 21-30 depict various views of another bone screw implant 10a fashioned in accordance with the present principles, characterized by the bone screw 12, a sleeve 14b and a set screw 50 (the sleeve and set screw forming a sleeve assembly). The bone screw implant 10a is the same as the bone screw implant 10 except for the incorporation of a secondary locking mechanism between the bone screw 12 and the sleeve/sleeve assembly 14b. As such, the features, characteristics, properties, and attributes of the bone screw 12 will not be re-discussed except where necessary and/or appropriate in describing the bone screw assembly 10a such as, but not limited to, describing the bone screw 12 relative to the sleeve/sleeve assembly 14b.

The sleeve 14b is the same as the sleeve 14 with the exception of the addition of threading 24 on its upper inside wall/bore 22 proximate the end 18. The bore 22 may be sized slightly larger than the bore 22 of the bone screw implant 10 to form an inner thread cavity 25 or its inner cavity may be sized the same. The sleeve assembly includes a set screw 50 that provides secondary locking of the sleeve 14b to the bone screw 12. The set screw 50 has a hexagonal side 51 (or other configuration for engagement with a set screw driver [not shown]). A bore 52 is disposed in the top 53 of the set screw 50 that allows engagement with an installation/de-installation tool (not shown). The set screw 50 also has a lower cylindrical wall 54 defining a cylindrical cavity 57. Threading 55 is provided on the outside of the annular wall 54. Threading 56 is also provided on the inside of the annular wall 54.

Once the sleeve 14b has been installed on the bone screw 12, the set screw 50 is installed. The set screw 50 is threaded into the annular cavity 25 formed between the outside of the upper section 32 of the bone screw 12 and the inside of the upper area of the sleeve 14b. Particularly, the annular wall 54 of the set screw 50 is received in the annular cavity 25. The inner threading 56 of the annular wall 54 of the set screw 50 engages the outer threading 37 of the bone screw 12, while the outer threading 55 of the annular wall 54 of the set screw 50 engages the inner threading 24 of the sleeve 14b. This couples the sleeve to the bone screw.

It should be readily grasped that the present bone screw implant is advantageous over the current state of the art.

What is claimed is:

1. A bone screw implant for sacroiliac joint fusion comprising:
   a bone screw defining a longitudinal axis and having external threading, a proximal end having sleeve engagement geometry, a distal end having a tip with a self-tapping geometry, external threading extending from the distal end to proximate the proximal end, and self-harvesting bone cutting geometry about the longitudinal axis that gathers and retains bone shavings produced by the bone cutting geometry; and
   a cylindrical sleeve having an external surface, a first end, a second end, a cylindrical bore extending from the first end to the second end and defining an internal surface, antirotation geometry on the external surface, and bone screw engagement geometry on the internal surface;
   wherein the anti-rotation geometry of the sleeve comprises tapered fins.

2. The bone screw implant of claim 1, wherein the self-tapping geometry of the tip comprises a plurality of cutting blades arranged about a central hole.

3. The bone screw implant of claim 2, wherein the self-harvesting bone cutting geometry comprises helical cutting flutes extending from the tip to adjacent the proximal end, the helical cutting flutes configured to produce bone graft during implantation of the bone screw.

4. The bone screw implant of claim 3, further comprising a plurality of widows in the helical cutting flutes, each one of the plurality of windows configured to receive and hold the bone shavings produced by the helical cutting flutes during implantation of the bone screw.

5. The bone screw implant of claim 4, wherein the plurality of windows are situated at various intervals about each helical cutting flute.

6. The bone screw implant of claim 5, wherein each one of the plurality of windows comprises a hole.

7. The bone screw implant of claim 6, wherein each hole is oval.

8. The bone screw implant of claim 5, wherein the plurality of windows comprise slots.

9. The bone screw implant of claim 5, wherein the plurality of windows are perpendicular with respect to the longitudinal axis.

10. The bone screw implant of claim 5, wherein the plurality of windows are angular with respect to the longitudinal axis.

11. The bone screw implant of claim 1, wherein:
the sleeve engagement geometry of the bone screw comprises a circumferential projection; and
the bone screw engagement geometry of the sleeve comprises a radial groove sized to receive the circumferential projection in a press-fit manner.

12. The bone screw implant of claim 11, wherein:
the radial projection comprises a circumferential ridge; and
the radial groove comprises a circumferential channel.

13. The bone screw implant of claim 12, wherein:
the sleeve engagement geometry of the proximal end of the bone screw further comprises first radial threading at an end of the proximal end; and
the bone screw engagement geometry of the sleeve further comprises second radial threading at a distal end of the sleeve.

14. The bone screw implant of claim 13, further comprising a set screw having:
external threading that provides engagement with the second radial threading; and
internal threading that provides engagement with the first radial threading.

15. A method of fusing a sacroiliac joint comprising:
providing a bone screw implant having:
a bone screw defining a longitudinal axis and having external threading, a proximal end having sleeve engagement geometry, a distal end having a tip with a self-tapping geometry, external threading extending front the distal end to proximate the proximal end, and self-harvesting bone cutting geometry about the longitudinal axis that gathers and retains bone shavings produced by the bone cutting geometry; and
a cylindrical sleeve having an external surface, a first end, a second end, a cylindrical bore extending from the first end to the second end and defining an internal surface, anti-rotation geometry on the external surface, wherein the anti-rotation geometry of the sleeve comprises tapered fins, and bone screw engagement geometry on the internal surface; and
installing the bone screw implant into the sacroiliac joint.

* * * * *